United States Patent
Winter et al.

(10) Patent No.: US 6,784,292 B2
(45) Date of Patent: Aug. 31, 2004

(54) METHOD FOR THE PRODUCTION OF IMIDAZO-(1,2-C)(2,3)-BENZODIAZEPINES AND INTERMEDIATES IN THE PRODUCTION THEREOF

(75) Inventors: Eric Winter, Braunschweig (DE); Matthias Schneider, Berlin (DE); Ulf Tilstam, Berlin (DE)

(73) Assignee: Schering AG, Berlin (DE)

( * ) Notice: Subject to any disclaimer, the term of this patent is extended or adjusted under 35 U.S.C. 154(b) by 8 days.

(21) Appl. No.: 10/344,156

(22) PCT Filed: Jul. 26, 2001

(86) PCT No.: PCT/EP01/08661

§ 371 (c)(1),
(2), (4) Date: Aug. 21, 2003

(87) PCT Pub. No.: WO02/12247

PCT Pub. Date: Feb. 14, 2002

(65) Prior Publication Data

US 2004/0019041 A1 Jan. 29, 2004

(30) Foreign Application Priority Data

Aug. 10, 2000 (DE) .......................................... 100 41 671

(51) Int. Cl.[7] .................. C07D 487/04; C07D 491/147; C07D 263/32; C07D 317/60; C07C 69/614
(52) U.S. Cl. ...................... 540/555; 540/562; 548/235; 549/349; 549/359; 549/436; 560/52
(58) Field of Search ................................. 540/555, 562; 548/235; 549/349, 359, 436; 560/52

(56) References Cited

U.S. PATENT DOCUMENTS 6,323,197 B1  11/2001  Csuzdi et al.
6,482,819 B1  11/2002  Abraham et al.

FOREIGN PATENT DOCUMENTS

WO    WO 9728163    8/1997
WO    WO 9906408    2/1999

OTHER PUBLICATIONS

F Gatta et al., "Derivatives of 2, 3–Benzodiazepine," IL Farmaco—Ed. Sc, 1985, pp. 942–955, vol. 40, XP002902060, Abstract.
H H Wasserman et al., "Oxazoles as masked activated carboxylates, Synthesis of (+)-di-o-methyl-culvularin," Tetrahedron Letters, 1981, pp. 4849–4852, vol. 22, No. 48, XP002902061, Abstract.
H H Wasserman et al., "Activated Carboxylates from the Photooxygenation of oxazoles," Tetrahedron, 1981, pp. 4059–4067, vol. 37, No. 23, XP002902062, Abstract.
Angela De Sarro et al., "Synthesis and anticonvulasant activity of new 2, 3–benzobiazepines as AMPA receptor antagonists," IL Farmaco, 1999, pp. 178–187, vol. 54, No. 3, XP002902063, Abstract.
Yan Wang et al., "Synthesis of 7,8–(methylenedioxy)–1–phenyl–3,5–dihydro–4H–2, 3–benzodiazepin–4–ones as novel and potent noncompetitive AMPA receptor antagonists," J. Med. Chem., 1998, pp. 2621–2625, vol. 41, No. 14, XP002902064, Abstract.
Angela De Sarro et al., "7,8–methylenedioxy–4H–2, 3–benzodiazepin–4–ones as novel AMPA receptor antagonists," Bioorganic & Medical Chemistry Letters, 1998, pp. 971–976, vol. 8, No. 8, XP002902065.
Gizella Abraham et al., "New Non Competetive AMPA Antagonists," Bioorganic & Medical Chemistry, 2000, pp. 2127–2143, vol. 8, No. 8, XP002902066, Abstract.

*Primary Examiner*—Evelyn Mei Huang
(74) *Attorney, Agent, or Firm*—Millen, White, Zelano & Branigan, P.C.

(57) ABSTRACT

The invention relates to a method for the preparation of compound of formula (1). The invention further relates to the previously unknown compounds of formulas (5 and 6) as intermediates in the production of benzodiazepines of formula (1).

8 Claims, No Drawings

METHOD FOR THE PRODUCTION OF IMIDAZO-(1,2-C)(2,3)-BENZODIAZEPINES AND INTERMEDIATES IN THE PRODUCTION THEREOF

This application is the 371 of PCT/EP01/08661, filed on Jul. 26, 2001.

The invention relates to a new process for the production of imidazo[1,2-c][2,3]benzodiazepines of general formula (1) as well as new intermediate products in the process,

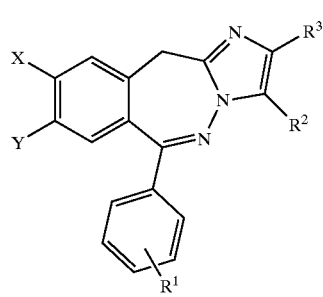

in which
$R^1$=hydrogen, $C_1$–$C_6$-alkyl, nitro, halogen, cyano, $C_1$–$C_4$-alkoxy, —$CF_3$, hydroxy or $C_1$–$C_6$-alkanoyloxy,
$R^2$ and $R^3$ are the same or different and mean hydrogen, halogen, $C_1$–$C_6$-alkoxy, hydroxy, cyano, $C_1$–$C_6$-alkanoyl, $C_2$–$C_6$-alkynyl, $C_2$–$C_6$-alkenyl; $C_1$–$C_6$-alkyl or $C_3$–$C_7$-cycloalkyl optionally substituted by halogen, hydroxy or $C_{1-6}$-alkoxy; or an aryl or hetaryl radical that is optionally substituted by halogen, $C_{1-4}$-alkoxy or $C_{1-4}$-alkyl,
X=hydrogen or halogen,
Y=$C_1$–$C_6$-alkoxy, or
X and Y together mean —O—$(CH_2)_n$—O— with n=1, 2 or 3.

The invention also contains, as new intermediate products for the production of pharmacologically active compounds, phenylacetic acid derivatives of general formula 5,

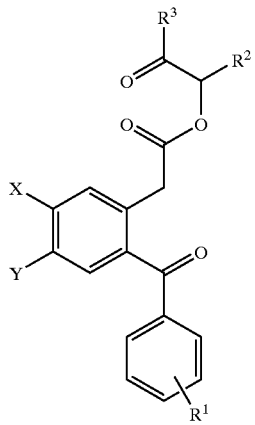

in which
$R^1$=hydrogen, $C_1$–$C_6$-alkyl, nitro, halogen, cyano, $C_1$–$C_4$-alkoxy, —$CF_3$, hydroxy or $C_1$–$C_6$-alkanoyloxy,
$R^2$ and $R^3$ are the same or different and mean hydrogen, halogen, $C_1$–$C_6$-alkoxy, hydroxy, cyano, $C_1$–$C_6$-alkanoyl, $C_2$–$C_6$-alkynyl, $C_2$–$C_6$-alkenyl; $C_1$–$C_6$-alkyl or $C_3$–$C_7$-cycloalkyl optionally substituted by halogen, hydroxy or $C_{1-6}$-alkoxy, or an aryl or hetaryl radical that is optionally substituted with halogen, $C_{1-4}$-alkoxy or $C_{1-4}$-alkyl,
X=hydrogen or halogen,
Y=$C_1$–$C_6$-alkoxy or
X and Y together mean —O—$(CH_2)_n$—O— with n=1, 2 or 3, and
oxazole derivatives of general formula 6,

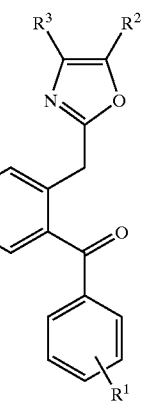

in which
$R^1$=hydrogen, $C_1$–$C_6$-alkyl, nitro, halogen, cyano, $C_1$–$C_4$-alkoxy, —$CF_3$, hydroxy or $C_1$–$C_6$-alkanoyloxy,
$R^2$ and $R^3$ are the same or different and mean hydrogen, halogen, $C_1$–$C_6$-alkoxy, hydroxy, cyano, $C_1$–$C_6$-alkanoyl, $C_2$–$C_6$-alkynyl, $C_2$–$C_6$-alkenyl; $C_1$–$C_6$-alkyl or $C_3$–$C_7$-cycloalkyl optionally substituted by halogen, hydroxy or $C_{1-6}$-alkoxy, or an aryl or hetaryl radical optionally substituted by halogen, $C_{1-4}$-alkoxy or $C_{1-4}$-alkyl,
X=hydrogen or halogen,
Y=$C_1$–$C_6$-alkoxy or
X and Y together mean —O—$(CH_2)_n$—O— with n=1, 2 or 3.

The radicals within the general formulas have the following meanings:

$C_1$–$C_6$-Alkyl is defined in each case as a straight-chain or branched alkyl radical, such as, for example, methyl, ethyl, propyl, isopropyl, butyl, isobutyl, sec-butyl, pentyl, isopentyl or hexyl.

$R^2$ and $R^3$ in the meaning of $C_2$–$C_6$-alkenyl contain, in each case, at least one double bond, such as, for example, vinyl, propenyl, buten-1-yl, isobutenyl, penten-1-yl, 2,2-dimethyl-buten-1-yl, 3-methylbuten-1-yl, or hexen-1-yl.

If $R^2$ and $R^3$ mean $C_1$–$C_6$-alkynyl, at least one triple bond is present, such as, for example, ethynyl, propynyl, butyn-1-yl, butyn-2-yl, pentyl-1-yl, pentyl-2-yl, 3-methylbutyn-1-yl, or hexyn-1-yl. The above-described alkenyl or alkinyl radicals can optionally also be substituted with halogen atoms. If a halogenated alkyl radical is present, the latter can be halogenated in one or more places, but can also be perhalogenated, such as, for example, —$CF_3$.

Within the above radicals, halogen is defined respectively as fluorine, chlorine, bromine and iodine.

$R^2$ and $R^3$ in the meaning of aryl and hetaryl radicals can optionally be substituted in one, two or three places with halogen, $C_{1-4}$-alkoxy-, or $C_{1-4}$-alkyl radicals; any permutations are possible.

The aryl and hetaryl radicals can be present as monocyclic or bicyclic compounds and contain 5–12 ring atoms, preferably 5–9 ring atoms, such as, for example, phenyl, biphenyl, naphthyl, or indenyl as an aryl radical, and thienyl, furyl, pyranyl, pyrrolyl, pyrazolyl, pyridyl, pyrimidyl, pyridazinyl, oxazolyl, isooxazolyl, thiazolyl, isothioazolyl, 1,3,4-oxadiazol-2-yl, 1,2,4-oxadiazol-5-yl, 1,2,4-oxadiazol-3-yl, quinolyl, isoquinolyl, benzo[1]thienyl, or benzofuranyl as a hetaryl radical, containing 1–3 heteroatoms, such as, for example, sulfur, oxygen, and/or nitrogen. As preferred radicals, 2-thienyl, 3-thienyl, pyridin-2-yl, pyridin-3-yl, pyridin-4-yl and phenyl can be mentioned.

With $R^2$ and $R^3$ in the meaning of $C_3$–$C_8$-cycloalkyl, for example, the cyclopropyl, cyclobutyl, cyclopentyl, cyclohexyl and cycloheptyl radicals are meant.

As $C_1$–$C_6$-alkanoyl radicals, in each case straight-chain or branched aliphatic carboxylic acid radicals, such as, for example, formyl, acetyl, propinoyl, butanoyl, isopropylcarbonyl, caproyl, valeroyl or trimethylacetyl, are suitable.

$R^1$ preferably means hydrogen, chlorine, nitro, methoxy; $R^2$ and $R^3$ preferably mean hydrogen, or $C_{1-4}$-alkyl or phenyl; X and Y together preferably mean —O—$CH_2$—O—.

Processes for the production of the compounds of general formula 1 are described within WO 97/28163.

The object of this invention is a new process for the synthesis of the compounds of general formula 1. Subjects of this invention are also new, previously unknown intermediate products of general formulas 5 and 6, which are processed within the framework of the synthesis and can be used per se or derivatized as starting materials for the synthesis of other target molecules.

This object is achieved by the teaching of the claims.

By the process according to the invention, fewer intermediate stages are processed than in the known synthesis from the prior art, the number of purification steps is significantly lower and the total yield is increased. The process according to the invention makes possible the production of the compounds of formula I on an industrial scale.

The invention thus contains a process for the production of imidazo[1,2-c][2,3]benzodiazepines of general formula 1
in which $R^1$, $R^2$ and $R^3$ as well as X and Y have the above meaning,
from phenylacetic acids of general formula 4,

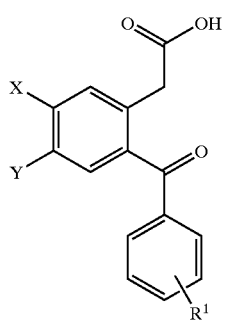

in which X, Y and $R^1$ have the above-mentioned meaning a) by esterification with an alcohol of Formula 5 a

to form phenylethyl acetate of general formula 5,

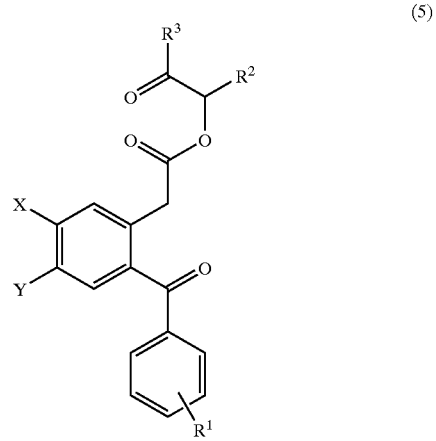

in which
X, Y, $R^1$, $R^2$ and $R^3$ have the above-mentioned meaning, b) by condensation with ammonia or an ammonia donor to form the oxazole of general formula 6,

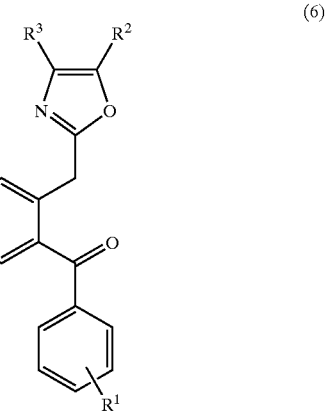

in which
X, Y, $R^1$, $R^2$ and $R^3$ have the above-mentioned meaning, and subsequent hydrazinolysis to form the compounds of general formula 1.

Imidazo[1,2-c][2,3]benzodiazepines of general formula 1 are synthesized according to Diagram 1.

Diagram 1

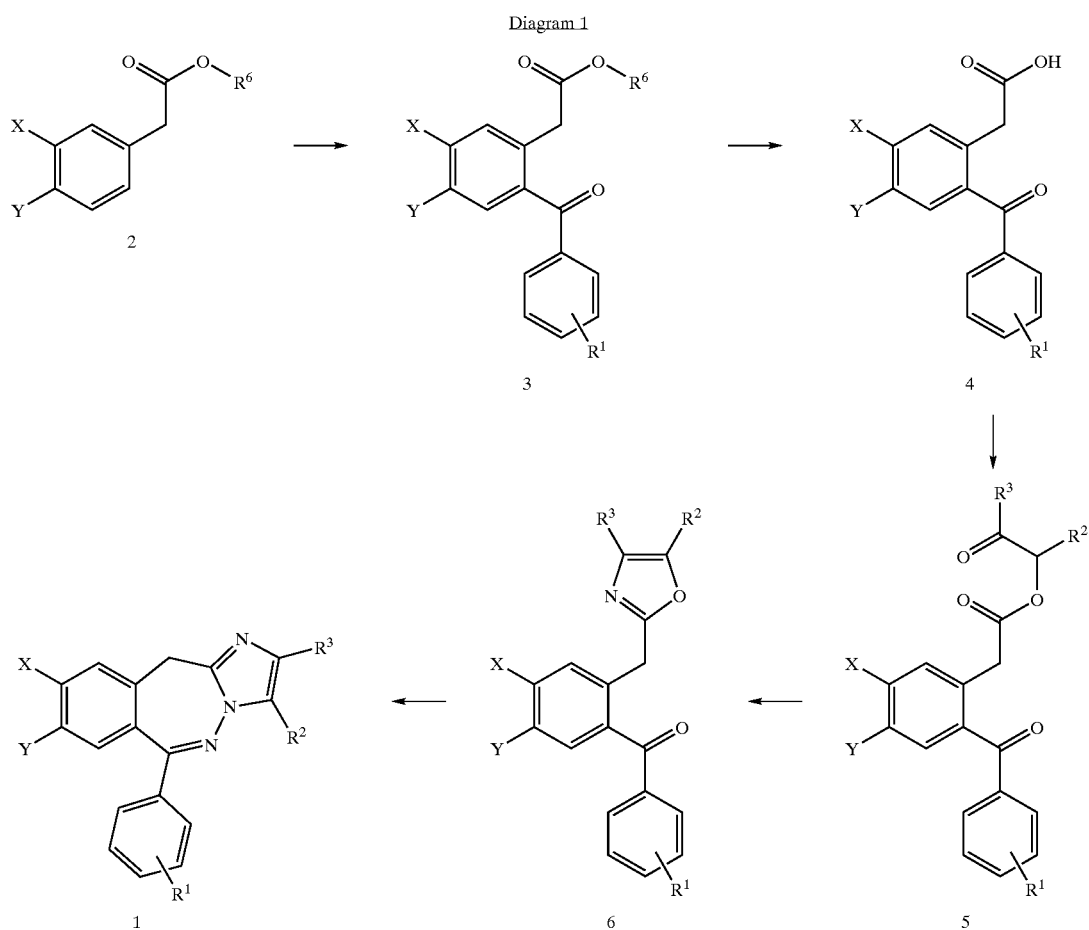

The reaction of a compound of general formula 2 to form a compound of general formula 3 is carried out according to a process that is known in the art (e.g., *J. Chem. Soc., Perkin Trans.* 1 1991, 169–173) of a Friedel-Crafts reaction. For example, compounds of general formula 2 are reacted in the presence of Lewis acids, such as, for example, tin tetrachloride, aluminum trichloride, titanium tetrachloride and an acylating agent, such as, for example, benzoyl chloride, benzoic acid anhydride or another activated carboxylic acid derivative. A significant increase in yield is achieved if additional N,N-dimethyl acetamide is added to the reaction mixture. As a solvent, halogenated hydrocarbons, such as, e.g., methylene chloride or ethylene chloride and mixtures thereof can be used. The reaction is performed in a temperature range of −30° to 50° C., but preferably in a temperature range of 0° to 25° C.

The reaction of a compound of general formula 3 to form a compound of general formula 4 is carried out according to a process of a saponification reaction that is known in the art. For example, a compound of general formula 3 is heated in the presence of a base, such as alkali hydroxide, but preferably sodium hydroxide, in a solvent, such as a lower, preferably primary alcohol or water or mixtures thereof. The reaction is performed in a temperature range of 25° to 150° C., but preferably in the temperature range of 70° to 110° C.

The reaction of a compound of general formula 4 to form a compound of formula 5 is carried out according to a process of an esterification that is known in the art. For example, a compound of general formula 4 is reacted in the presence of an activating reagent, such as, e.g., carbonyldiimidazole, and an alcohol of formula

(5a)

such as 3-hydroxy-2-butanone. As solvents, halogenated hydrocarbons, such as, e.g., methylene chloride or ethylene chloride, as well as THF and mixtures thereof can be used. The reaction is performed in a temperature range of −20° to 100° C., but preferably in a temperature range of 0° to 25° C.

It is familiar to one skilled in the art that $R^2$ and $R^3$ can be varied in compounds of general formula 5 according to standard methods. This can take place by use of other alcohols in the esterification step, but also by reesterification of an ester that is already present. $R^2$ and $R^3$ can thus have the meaning of hydrogen, halogen, alkoxy, hydroxy, cyano, alkanoyl, optionally substituted alkynyl, optionally substituted alkenyl; alkyl or cycloalkyl that is optionally substituted by halogen, hydroxy, or alkoxy; or an optionally substituted aryl or hetaryl radical.

The reaction of a compound of general formula 5 to form a compound of general formula 6 is carried out according to a process, known in the art, for the production of oxazoles by condensation of two carbonyl groups with ammonia. For example, a compound of general formula 5 is reacted in the presence of ammonium acetate, ammonia, an ammonia solution or another ammonia donor, such as, e.g., acetamide or formamide in the presence of acetic acid. As solvents, halogenated hydrocarbons, such as, e.g., methylene chloride or ethylene chloride; organic acids, such as e.g., formic acid or acetic acid, as well as lower alcohols, such as, e.g., methanol or ethanol, but also ethylene glycol and mixtures thereof, can be used. The reaction is performed in a temperature range of 0° to 150° C., but preferably in a temperature range of 50° to 100° C.

The reaction of a compound of general formula 6 to form a compound of general formula 1 is carried out according to a process, known in the art, by hydrazinolysis or hydrazone formation. For example, a compound of general formula 6 is reacted in the presence of hydrazine or hydrazine-hydrate. As solvents, halogenated hydrocarbons, such as, e.g., methylene chloride or ethylene chloride, organic acids, such as, e.g., formic acid or acetic acid, as well as lower alcohols, such as, e.g., methanol or ethanol, but also ethylene glycol and mixtures thereof, are used. The reaction is performed in a temperature range of 0° to 200° C., but preferably in a temperature range of 80° to 120° C. A reaction scheme in an autoclave is possible.

The reaction of a compound of general formula 5 to form a compound of formula 1 is also carried out in a single-pot reaction. For example, a compound of formula 5 is reacted in the presence of ammonium acetate, ammonia, an ammonia solution or another ammonia donor, such as, e.g., acetamide or formamide in the presence of acetic acid. As solvents, halogenated hydrocarbons, such as, e.g., methylene chloride or ethylene chloride; organic acids, such as, e.g., formic acid or acetic acid, as well as lower alcohols, such as, e.g., methanol or ethanol; but also ethylene glycol and mixtures thereof can be used. The reaction is performed in a temperature range of 0° to 150° C., but preferably in a temperature range of 50° to 100° C. After the reaction is completed, hydrazine or hydrazine-hydrate is added to the reaction mixture. The reaction is performed in a temperature range of 0° to 200° C., but preferably in a temperature range of 80° to 120° C. A reaction scheme in an autoclave is possible.

If the production of the starting compounds is not described, the latter are known or can be produced analogously to known processes or to processes that are described here. Below, the process according to the invention is depicted by way of example.

EXAMPLES

2-Benzoyl-4,5-(methylenedioxy)-phenylacetic Acid Methyl Ester (3)

79 ml of tin tetrachloride and 25 ml of N,N'-dimethylacetamide in 270 ml of methylene chloride are mixed at room temperature with 39 ml of benzoyl chloride. 44 g of 4,5-(methylenedioxy)-phenylacetic acid methyl ester (2) is added in drops to this mixture at 0° C., and the solution is stirred for 12 hours at room temperature. For the purpose of working-up, the addition of 660 ml of water at −15° C. as well as an extraction of the aqueous phase with methylene chloride follow. The collected organic fractions are washed with 6N aqueous NaOH and completely concentrated by evaporation in a rotary evaporator. Crude product 3 (74 g) is crystallized from ethanol.

$^1$H-NMR (CDCl$_3$): δ=3.61 (s, 3 H, OMe), 3.80 (s, 2 H, benzyl. CH$_2$), 6.03 (s, 2 H, OCH$_2$O), 6.84 and 6.88 (2 s to 1 H, 3- and 6-H aryl), 7.43–7.80 (m, 5 H, PhCO).

Melting point: 74–76° C., combustion analysis: Cld. C 68.45 H 4.73
                                                Fnd. C 68.53 H 4.59

Produced analogously are:

2-(4-Chloro-benzoyl)-4,5-(methylenedioxy)-phenylacetic acid methyl ester 2-(4-Nitro-benzoyl)-4,5-(methylenedioxy)-phenylacetic acid methyl ester 2-(4-Methoxy-benzoyl)-4,5-(methylenedioxy)-phenylacetic acid methyl ester 2-(4-Methyl-benzoyl)-4,5-(methylenedioxy)-phenylacetic acid methyl ester 2-(4-Cyano-benzoyl)-4,5-(methylenedioxy)-phenylacetic acid methyl ester 2-Benzoyl-4,5-(methylenedioxy)-phenylacetic Acid (4)

A suspension of 10 g of 2 in 50 ml of 1N aqueous NaOH is refluxed for 2 hours. Then, 10 ml of 1N aqueous sulfur acid is added, and the precipitating solid is filtered off and rewashed with water. Product 4 (8.3 g) is dried i.v. and used without further purification in the next stage.

$^1$H-NMR (DMSO): δ=3.68 (s, 2 H, benzyl. CH$_2$), 6.12 (s, 2 H, OCH$_2$O), 6.86 and 7.03 (2 s to 1 H, 3- and 6-H aryl), 7.50–7.73 (m, 5 H, PhCO), 12.18 (br. s, 1 H, COOH).

Melting point: 185–189° C., combustion analysis: Cld. C 67.60 H 4.25
                                                  Fnd. C 67.66 H 4.20

Produced analogously are:

2-(4-Chloro-benzoyl)-4,5-(methylenedioxy)-phenylacetic acid 2-(4-Nitro-benzoyl)-4,5-(methylenedioxy)-phenylacetic acid 2-(4-Methoxy-benzoyl)-4,5-(methylenedioxy)-phenylacetic acid 2-(4-Methyl-benzoyl)-4,5-(methylenedioxy)-phenylacetic acid 2-(4-Cyano-benzoyl)-4,5-(methylenedioxy)-phenylacetic acid 2-Benzoyl-4,5-(methylenedioxy)-phenylacetic Acid-(3-oxo-but-2-ylester) (5)

50 g of 4, 19 g of 3-hydroxy-2-butanone and 32 g of N,N'-carbonyldiimidazole are dissolved at room temperature in 500 ml of methylene chloride and stirred for 3 days. For working-up, it is mixed with 200 ml of VE-water and then extracted with methylene chloride. The collected organic fractions are concentrated by evaporation in a rotary evaporator. The crude product is crystallized from methanol (2×), and 45 g of 5 is obtained.

$^1$H-NMR (CDCl$_3$): δ=1.32 (d, 3 H, J=6.9, CH$_3$C—O), 2.11 (s, 3 H, CH$_3$C=O), 3.88 (s, 2 H, benzyl. CH$_2$), 5.03 (q, 1 H, J=6.9, CH—O), 6.04 (s, 2 H, OCH$_2$O), 6.87 and 6.90 (2 s to 1 H, 3- and 6-H aryl), 7.42–7.74 (m, 5 H, PhCO).

| | | |
|---|---|---|
| Melting point: 81–83° C., combustion analysis: | Cld. C 67.79 | H 5.12 |
| | Fnd. C 67.83 | H 5.04 |

Produced analogously are:

2-(4-Chloro-benzoyl)-4,5-(methylenedioxy)-phenylacetic acid-(3-oxo-but-2-ylester)

2-(4-Nitro-benzoyl)-4,5-(methylenedioxy)-phenylacetic acid-(3-oxo-but-2-ylester)

2-(4-Methoxy-benzoyl)-4,5-(methylenedioxy)-phenylacetic acid-(3-oxo-but-2-ylester)

2-Benzoyl-4,5-(methylenedioxy)-phenylacetic acid-(4-oxo-hex-3-ylester)

2-Benzoyl-4,5-(methylenedioxy)-phenylacetic acid-(2-oxo-1,2-diphenyl-eth-1-ylester)

2-Benzoyl-4,5-(methylenedioxy)-benzyl-4,5-dimethyl-oxazole (6)

14 ml of concentrated acetic acid is added to 10 g of 5 and 19 g of ammonium acetate in 200 ml of 1,2-dichlorethane, and the mixture is refluxed for 6 hours. Then, 100 ml of 1N aqueous NaOH is added, and it is extracted with methylene chloride. The combined organic extracts are concentrated by evaporation in a rotary evaporator, and the crude product is filtered on silica gel (hexane:ethyl acetate 9:1→8:2). 6.9 g of pure 6 is obtained (viscous oil).

$^1$H-NMR (CDCl$_3$): δ=1.94 and 2.03 (2 s to 3 H, 2 CH$_3$), 4.13 (s, 2 H, benzyl, CH$_2$), 6.01 (s, 2 H, OCH$_2$O), 6.83 and 6.86 (2 s to 1 H, 3- and 6-H aryl), 7.41–7.80 (m, 5 H, PhCO).

| | | | |
|---|---|---|---|
| Combustion analysis: | Cld. C 71.63 | H 5.11 | N 4.18 |
| | Fnd. C 71.47 | H 5.04 | N 3.97 |

Produced analogously are:

2-(4-Chloro-benzoyl)-4,5-(methylenedioxy)-benzyl-4,5-dimethyl-oxazole 2-(4-Nitro-benzoyl)-4,5-(methylenedioxy)-benzyl-4,5-dimethyl-oxazole 2-(4-Methoxy-benzoyl)-4,5-(methylenedioxy)-benzyl-4,5-dimethyl-oxazole 2-Benzoyl-4,5-(methylenedioxy)-benzyl-4,5-diethyl-oxazole 2-Benzoyl-4,5-(methylenedioxy)-benzyl-4,5-diphenyl-oxazole 2,3-Dimethyl-6-phenyl-(12H)-[1,3]dioxolo[4,5-h]imidazo[1,2-c][2,3]benzodiazepine (1)

In an autoclave, 0.5 ml of hydrazine-hydrate is added to 2 g of 6, dissolved in 18 ml of ethylene glycol and 2 ml of concentrated acetic acid. It is heated for 12 hours to 120° C., and then the reaction mixture is mixed at room temperature with 2N aqueous NaOH. It is extracted several times with ethyl acetate, and the combined organic phases are completely concentrated by evaporation in a rotary evaporator. The crude product is purified by column chromatography (hexane: ethyl acetate 9:1→8:2), and the yield of pure 1 is 1.2 g.

$^1$H-NMR (DMSO): δ=2.01 and 2.20 (2 s to 3 H, 2 CH$_3$), 3.82 (br. s, 2 H, benzyl, CH$_2$), 6.08 (s, 2 H, OCH$_2$O), 6.55 and 7.15 (2 s to 1 H, 2 aryl-H), 7.48–7.72 (m, 5 H, PhCO).

| | | | |
|---|---|---|---|
| Melting point: 177° C., combustion analysis: | Cld. C 72.49 | H 5.18 | N 12.88 |
| | Fnd. C 72.33 | H 5.31 | N 12.46 |

Produced Analogously are:

2,3-Dimethyl-6-(4-chloro-phenyl)-(12H)-[1,3]dioxolo[4,5-h]imidazo[1,2-c][2,3] benzodiazepine 2,3-Dimethyl-6-(4-nitro-phenyl)-(12H)-[1,3]dioxolo[4,5-h]imidazo[1,2-c][2,3] benzodiazepine 2,3-Dimethyl-6-(4-methoxy-phenyl)-(12H)-[1,3]dioxolo[4,5-h]imidazo[1,2-c][2,3] benzodiazepine 2,3-Diethyl-6-phenyl-(12H)-[1,3]dioxolo[4,5-h]imidazo[1,2-c][2,3]benzodiazepine 2,3-Diphenyl-6-phenyl-(12H)-[1,3]dioxolo[4,5-h]imidazo[1,2-c][2,3]benzodiazepine

What is claimed is:

1. A process for the production of imidazo[1,2-c][2,3]benzodiazepines of formula (1)

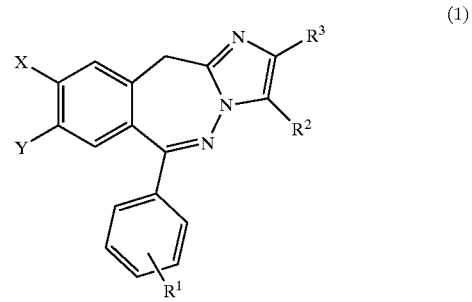

in which

R$^1$=is hydrogen, C$_1$–C$_6$-alkyl, nitro, halogen, cyano, C$_1$–C$_4$-alkoxy, —CF$_3$, hydroxy or C$_1$–C$_6$-alkanoyloxy, R$^2$ and R$^3$ are the same or different and mean hydrogen, halogen, C$_1$–C$_6$-alkoxy, hydroxy, cyano, C$_1$–C$_6$-alkanoyl, C$_2$–C$_6$-alkynyl, C$_2$–C$_6$-alkenyl; C$_1$–C$_6$-alkyl or C$_3$–C$_7$-cycloalkyl which in each case is unsubstituted or substituted by halogen, hydroxy or C$_{1-6}$-alkoxy, or an aryl or hetaryl radical which in each case is unsubstituted or substituted by halogen, C$_{1-4}$-alkoxy or C$_{1-4}$-alkyl, X=is hydrogen or halogen,
Y=is $C_1$–$C_6$-alkoxy, or
X and Y together mean —O—$(CH_2)_n$—O—, and
n=is 1, 2 or 3,
from a phenylacetic acids of formula (4),

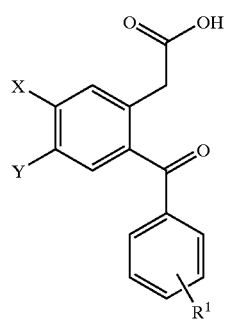

(4)

which process comprises:
a) esterifying the phenylacetic and with an alcohol of formula (5a)

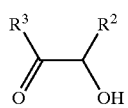

(5a)

to form a phenylethyl acetate of formula (5)

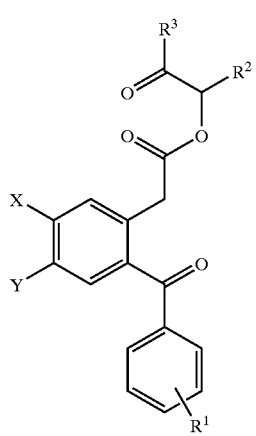

(5)

b) condensing the phenylethyl acetate with ammonia or an ammonia donor to form an oxazole of formula (6)

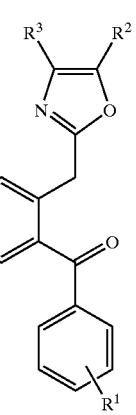

(6)

c) hydrazinolyzing the oxazole to form the compounds of general formula (1)

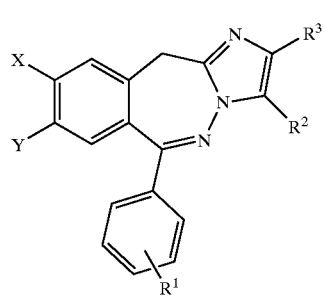

(1)

2. A process according to claim 1, wherein compounds of general formula (5) is reacted using a single-pot reaction by reaction in the presence of ammonium acetate and ammonia or an ammonia donor at 0–150° C. in the solvent or solvent mixtures and then with hydrazine at 0–200° C.

3. A process according to claim 1, wherein the compound of formula produced is: 2,3-dimethyl-6-phenyl-(12H)-[1,3] dioxolo[4,5-h]imidazo[1,2-c][2,3]benzodiazepine;

2,3-Dimethyl-6-(4-chloro-phenyl)-(12H)-[1,3]dioxolo[4, 5-h]imidazo[1,2-c][2,3] benzodiazepine;

2,3-Dimethyl-6-(4-nitro-phenyl)-(12H)-[1,3]dioxolo[4,5-h]imidazo[1,2-c][2,3] benzodiazepine;

2,3-Dimethyl-6-(4-methoxy-phenyl)-(12H)-[1,3]dioxolo [4,5-h]imidazo[1,2-c][2,3]benzodiazepine;

2,3-Diethyl-6-phenyl-(12H)-[1,3]dioxolo[4,5-h]imidazo [1,2-c][2,3]benzodiazepine; or 2,3-Diphenyl-6-phenyl-(12H)-[1,3]dioxolo[4,5-h] imidazo[1,2-c][2,3]benzodiazepine.

4. A phenylacetic acid ester of formula 5,

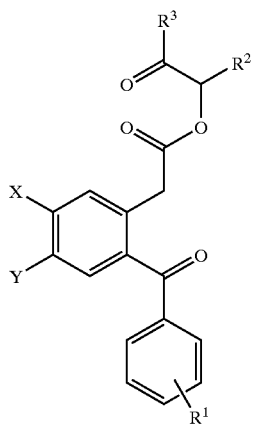

in which
R$^1$=is hydrogen, C$_1$–C$_6$-alkyl, nitro, halogen, cyano, C$_1$–C$_4$-alkoxy, —CF$_3$, hydroxy or C$_1$–C$_6$-alkanoyloxy,
R$^2$ and R$^3$ are the same or different and mean hydrogen, halogen, C$_1$–C$_6$-alkoxy, hydroxy, cyano, C$_1$–C$_6$-alkanoyl, C$_2$–C$_6$-alkynyl, C$_2$–C$_6$-alkenyl; C$_1$–C$_6$-alkyl or C$_3$–C$_7$-cycloalkyl which in each case is unsubstituted or substituted by halogen, hydroxy or C$_{1-6}$-alkoxy; or an aryl or hetaryl radical which in each case is unsubstituted or substituted by halogen, C$_{1-4}$-alkoxy or C$_{1-4}$-alkyl,
X=is hydrogen or halogen,
Y=C$_1$–C$_6$-alkoxy, or
X and Y together mean —O—(CH$_2$)$_n$—O—, and
n=is 1, 2 or 3.

5. An oxazole compound of formula 6,

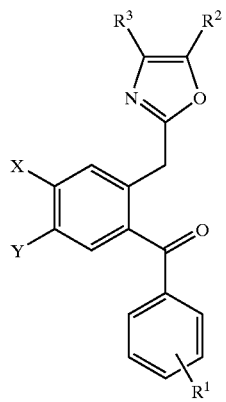

in which
R$^1$=is hydrogen, C$_1$–C$_6$-alkyl, nitro, halogen, cyano, C$_1$–C$_4$-alkoxy, —CF$_3$, hydroxy or C$_1$–C$_6$-alkanoyloxy,
R$^2$ and R$^3$ are the same or different and mean hydrogen, halogen, C$_1$–C$_6$-alkoxy, hydroxy, cyano, C$_1$–C$_6$-alkanoyl, C$_2$–C$_6$-alkynyl, C$_2$–C$_6$-alkenyl; C$_1$–C$_6$-alkyl or C$_3$–C$_7$-cycloalkyl o which in each case is unsubstituted or substituted by halogen, hydroxy or C$_{1-6}$-alkoxy; or an aryl or hetaryl radical which in each case is unsubstituted or substituted by halogen, C$_{1-4}$-alkoxy or C$_{1-4}$-alkyl,
X=is hydrogen or halogen,
Y=is C$_1$–C$_6$-alkoxy or
X and Y together mean —O—(CH$_2$)$_n$—O—, and
n=1, 2 or 3.

6. The process of claim 2, wherein the single-pot reaction is conducted in an autoclave.

7. A process according to claim 2, wherein the compound of formula (1) produced is:
   2,3-Dimethyl-6-phenyl-(12H)-[1,3]dioxolo[4,5-h]imidazo[1,2-c][2,3]benzodiazepine;
   2,3-Dimethyl-6-(4-chloro-phenyl)-(12H)-[1,3]dioxolo[4,5-h]imidazo[1,2-c][2,3]benzodiazepine;
   2,3-Dimethyl-6-(4-nitro-phenyl)-(12H)-[1,3]dioxolo[4,5-h]imidazo[1,2-c][2,3]benzodiazephine;
   2,3-Dimethyl-6-(4-methoxy-phenyl)-(12H)-[1,3]dioxolo[4,5-h]imidazo[1,2-c][2,3]benzodiazepine;
   2,3-Dimethyl-6-phenyl-(12H)-[1,3]dioxolo[4,5-h]imidazo[1,2-c][2,3]benzodiazepine; or
   2,3-Dimethyl-6-phenyl-(12H)-[1,3]dioxolo[4,5-h]imidazo[1,2-c][2,3]benzodiazepine.

8. A process according to claim 6, wherein the compound of formula (1) produced is:
   2,3-Dimethyl-6-phenyl-(12H)-[1,3]dioxolo[4,5-h]imidazo[1,2-c][2,3]benzodiazepine;
   2,3-Dimethyl-6-(4-chloro-phenyl)-(12H)-[1,3]dioxolo[4,5-h]imidazo[1,2-c][2,3]benzodiazepine;
   2,3-Dimethyl-6-(4-nitro-phenyl)-(12H)-[1,3]dioxolo[4,5-h]imidazo[1,2-c][2,3]benzodiazepine;
   2,3-Dimethyl-6-(4-methoxy-phenyl)-(12H)-[1,3]dioxolo[4,5-h]imidazo[1,2-c][2,3]benzodiazepine;
   2,3-Dimethyl-6-phenyl-(12H)-[1,3]dioxolo[4,5-h]imidazo[1,2-c][2,3]benzodiazepine; or
   2,3-Dimethyl-6-phenyl-(12H)-[1,3]dioxolo[4,5-h]imidazo[1,2-c][2,3]benzodiazepine.

* * * * *